US008235926B2

(12) United States Patent
Houchin

(10) Patent No.: US 8,235,926 B2
(45) Date of Patent: Aug. 7, 2012

(54) BRACE FOR RESTRAINING SHOULDER MOVEMENT

(76) Inventor: Todd Houchin, Campbellsburg, IN (US)

( * ) Notice: Subject to any disclaimer, the term of this patent is extended or adjusted under 35 U.S.C. 154(b) by 1042 days.

(21) Appl. No.: 11/474,560

(22) Filed: Jun. 26, 2006

(65) Prior Publication Data

US 2007/0299381 A1    Dec. 27, 2007

(51) Int. Cl.
*A61F 5/00* (2006.01)
(52) U.S. Cl. ............ 602/20; 602/5; 128/869; 128/875; 128/878
(58) Field of Classification Search ............... 2/455, 44, 2/45; 602/19, 4, 70, 5, 20; 128/882, 869, 128/98.1, 874–878
See application file for complete search history.

(56) References Cited

U.S. PATENT DOCUMENTS

| 1,961,515 A * | 6/1934 | Friedman ............... 604/392 |
| 3,010,452 A | 11/1961 | Smith |
| 3,188,090 A | 6/1965 | Job |
| 3,324,851 A | 6/1967 | Posner |
| 3,970,316 A * | 7/1976 | Westmoreland, Jr. ........ 473/212 |
| 4,061,340 A | 12/1977 | Husted |
| 4,610,244 A * | 9/1986 | Hammond ............... 128/876 |
| 4,860,560 A * | 8/1989 | Lundelius ............... 70/16 |
| 5,063,941 A | 11/1991 | White |
| 5,538,015 A * | 7/1996 | Paulson ............... 128/869 |
| 5,538,499 A | 7/1996 | Schwenn et al. |
| 5,665,058 A | 9/1997 | Young |
| 5,717,997 A * | 2/1998 | Garcia ............... 2/23 |
| 6,146,346 A | 11/2000 | Godwin |
| 6,152,891 A | 11/2000 | Carlson |
| 6,322,528 B1 | 11/2001 | Kania |
| 6,443,920 B1 * | 9/2002 | Clement ............... 602/62 |
| 6,709,411 B1 | 3/2004 | Olinger |
| 6,733,467 B2 | 5/2004 | Kania |
| 6,935,342 B2 * | 8/2005 | Larson ............... 128/869 |
| 7,954,497 B2 * | 6/2011 | Doroski ............... 128/878 |
| 2006/0179545 A1 * | 8/2006 | Arensdorf et al. ........ 2/227 |
| 2007/0027419 A1 * | 2/2007 | Drennan ............... 602/19 |

* cited by examiner

*Primary Examiner* — Kim M Lewis
(74) *Attorney, Agent, or Firm* — Maginot, Moore & Beck LLP

(57) ABSTRACT

A shoulder brace comprises a girdle, at least one tether connected to the girdle, and an arm band connected to the at least one tether. In one embodiment, the girdle includes at least one pad holder in the form of a pocket. The at least one tether is fastened at one end to the girdle. The opposite end of the tether is fastened to an arm band. The arm band of the brace may be provided as part of a separate flexible strip of material or may be integral with the opposite end of the tether. The arm band is fashioned to wrap around the arm of an athlete. With the tether secured to both the girdle and the arm band, the range of movement of the athlete's arm and shoulder is restricted.

19 Claims, 4 Drawing Sheets

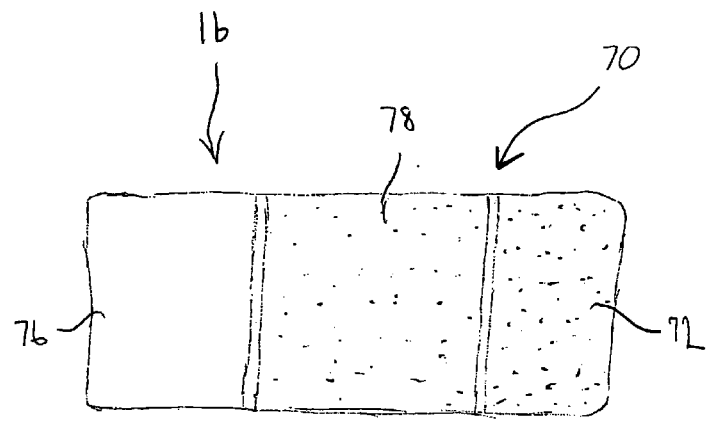
FIG. 4
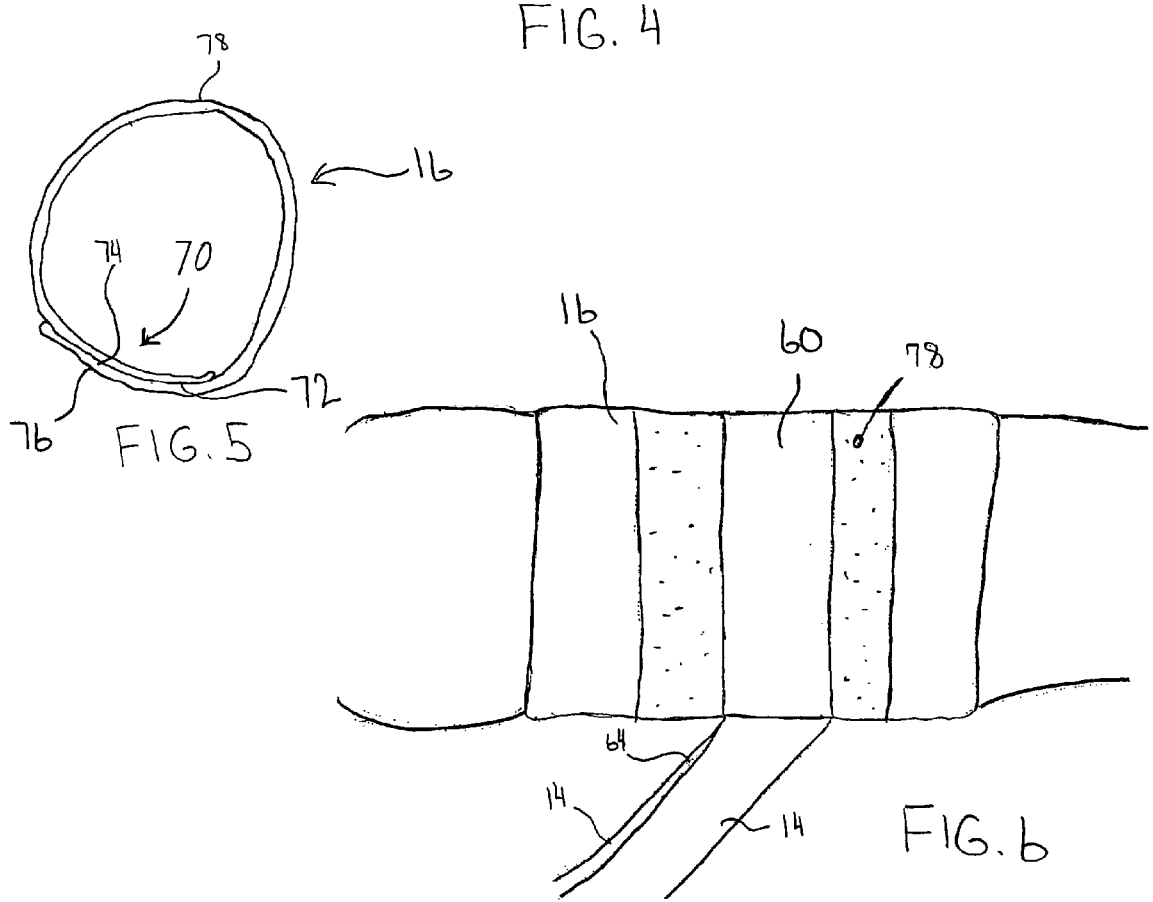
FIG. 5
FIG. 6

BRACE FOR RESTRAINING SHOULDER MOVEMENT

FIELD

This invention relates to the field of shoulder stabilization and protection, and particularly to shoulder braces that restrict movement of the arm in order to stabilize and prevent further injury to the shoulder.

BACKGROUND

Injuries are common to those participating in athletic activities. Some injuries are serious enough to completely prevent participation in a particular sport for some time. However, other injuries are more minor in nature, and an athlete may be allowed to participate in the sport while nursing the injury. In these situations where an injured athlete continues to participate in a sport, protective measures are often taken to prevent further injury to the athlete. To this end, athletes often wear various pads, braces, or restraints to prevent aggravation of an injury.

A shoulder injury is one common type of injury that may result from athletic activity. When an athlete injures his or her shoulder, various forms of shoulder pads, braces, restraints, and related protective measures are available to the athlete. Use of these protective measures may allow the athlete to continue to participate in a sport while the injury continues to heal.

One sport where shoulder injuries are common is in the sport of football. Many football players continue to play football while nursing a shoulder injury. Various protective measures are available to football players with shoulder injuries. For example, a common shoulder brace available to football players includes a belt worn about the chest of the player. With this brace, arm bands are connected to the chest belt. The arm bands restrict movement of the arms and shoulders, thus preventing the player from making an extreme arm movement that might aggravate the shoulder injury. Unfortunately, this type of shoulder brace that includes a chest strap may be uncomfortable for the player. In particular, when the player's heart rate increases, the chest belt may make breathing uncomfortable. When the belt is too tight around the chest, expansion of the chest is restricted, thus preventing the necessary heavy breathing needed to supply the athlete with proper amounts of oxygen. Furthermore, repeated expansion and contraction of the chest may loosen the belt or cause it to move on the chest, thus changing the degree of movement available to the athlete wearing the brace.

While not all shoulder braces include a chest belt, other shoulder braces present other problems for football players. For example, some shoulder braces are configured for use with a belt. These shoulder braces tend to ride up on the player's torso and/or create a wedge effect on the player's pants. Other shoulder braces are too restrictive and do not allow a necessary minimal degree of arm movement needed by the player, depending upon the position played. As another example, some shoulder braces are not compatible with football uniforms and pads, making the braces difficult or impossible to wear in conjunction with the required gear.

Accordingly, it would be desirable to provide a shoulder brace designed in such a way that it is particularly useful for football players and other athletes. Such a shoulder brace would be compatible for use with football uniforms and pads. Such a shoulder brace would also be comfortable and would not restrict heavy breathing by the player. In addition, such a shoulder brace would provide the football player with significant degrees of shoulder movement, thus allowing the athlete to continue to play football with only the necessary restrictions.

SUMMARY

A shoulder brace comprises a girdle, at least one tether connected to the girdle, and an arm band connected to the at least one tether. The girdle is designed as a pant and includes a crotch portion. In one embodiment, the girdle includes at least one pad holder in the form of a pocket. Another pocket is configured to retain an athletic cup. The girdle also includes reinforced portions.

The at least one tether is fastened at one end to the girdle. In one embodiment the tether is fastened along the side of the girdle to a reinforced portion of the girdle. The tether is generally 10 inches or more in length. In one embodiment the length of the tether is adjustable. Furthermore, two or more tethers may extend from a side of the girdle to the arm band.

The arm band of the brace may be provided as part of a separate flexible strip of material or may be integral with the end of the tether. The arm band is fashioned to wrap around the arm of an athlete. The arm band includes a fastener to secure the arm band to the arm of the athlete. If the arm band is separate from the tether, means are provided for fastening the tether to the arm band, thus securing the tether to the arm band.

With the tether secured to both the girdle and the arm band, the range of movement of the athlete's arm and shoulder is restricted. Accordingly, the shoulder brace is used to prevent an athlete from further aggravating an injury to the shoulder.

BRIEF DESCRIPTION OF THE DRAWINGS

FIG. 4 shows an arm band of the shoulder brace of FIG. 1;

FIG. 5 shows a cross-sectional view of the arm band of FIG. 4 when positioned on a human arm; and FIG. 6 shows a side view of the arm band of FIG. 4 positioned on a human arm.

DESCRIPTION

Figure 1:
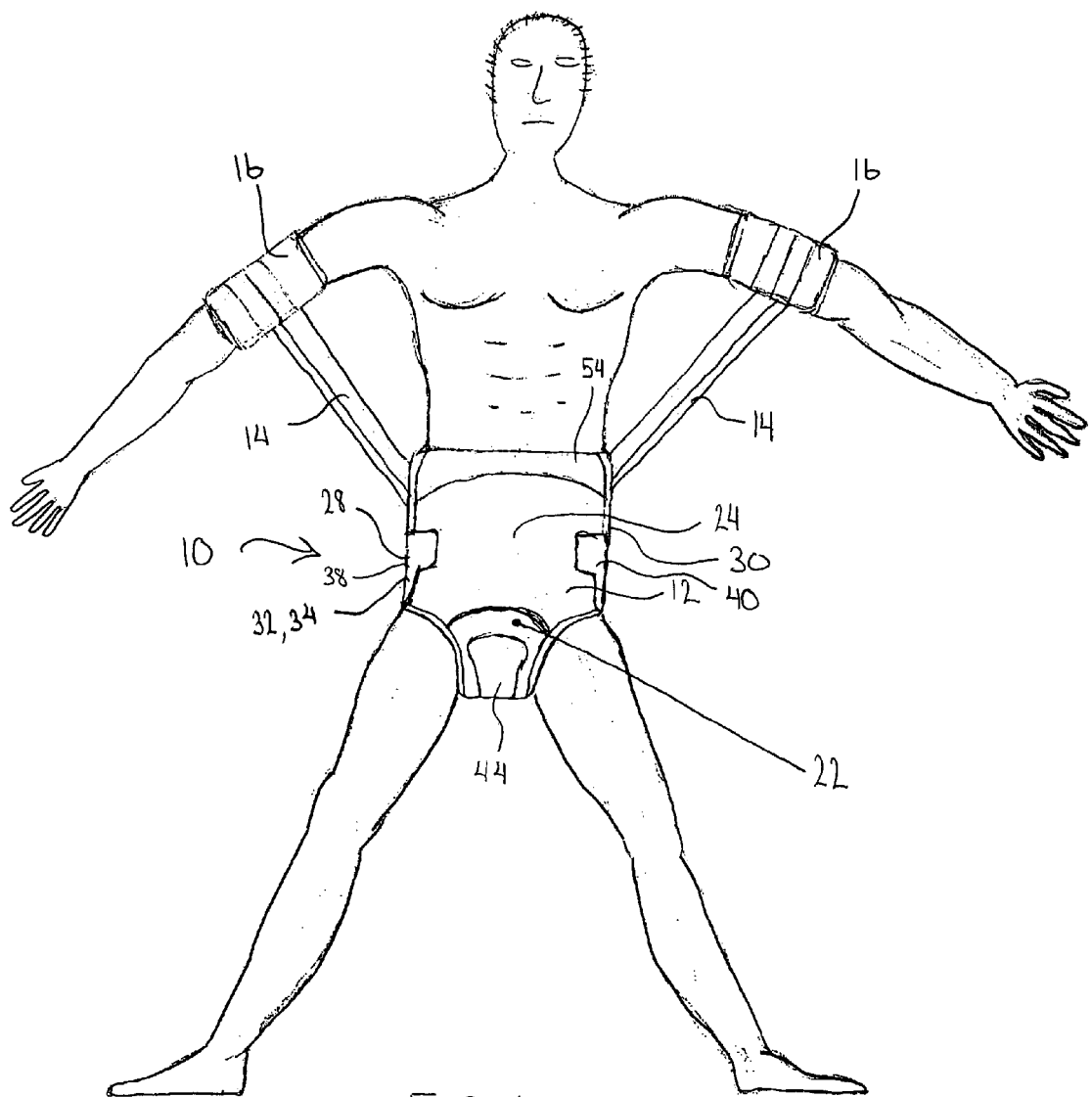
FIG. 1 shows a shoulder brace positioned on a human in order to restrict movement of the arms and shoulders of the human.

With reference to FIG. 1, a shoulder brace 10 is shown positioned on a human. The shoulder brace 10 generally comprises a girdle 12 configured to be worn by the human. A plurality of tethers 14 are connected to the girdle 12. Each tether 14 includes one end connected to the girdle 12 and an opposite end connected to an arm band 16. The arm bands 16 encircle the upper portion of the arm where the human's biceps are located. As shown in FIG. 1, the tethers 14 prohibit the arm bands 16 from moving a defined distance from the girdle 12, thus restricting movement of the arms and shoulders.

Figure 2:
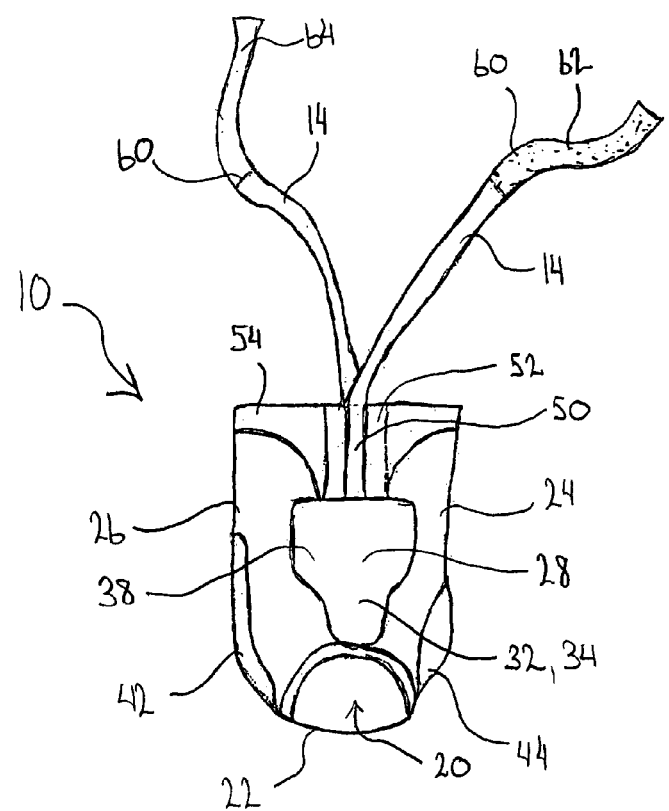
FIG. 2 shows a side view of the shoulder brace of FIG. 1 removed from the human.
Figure 3:
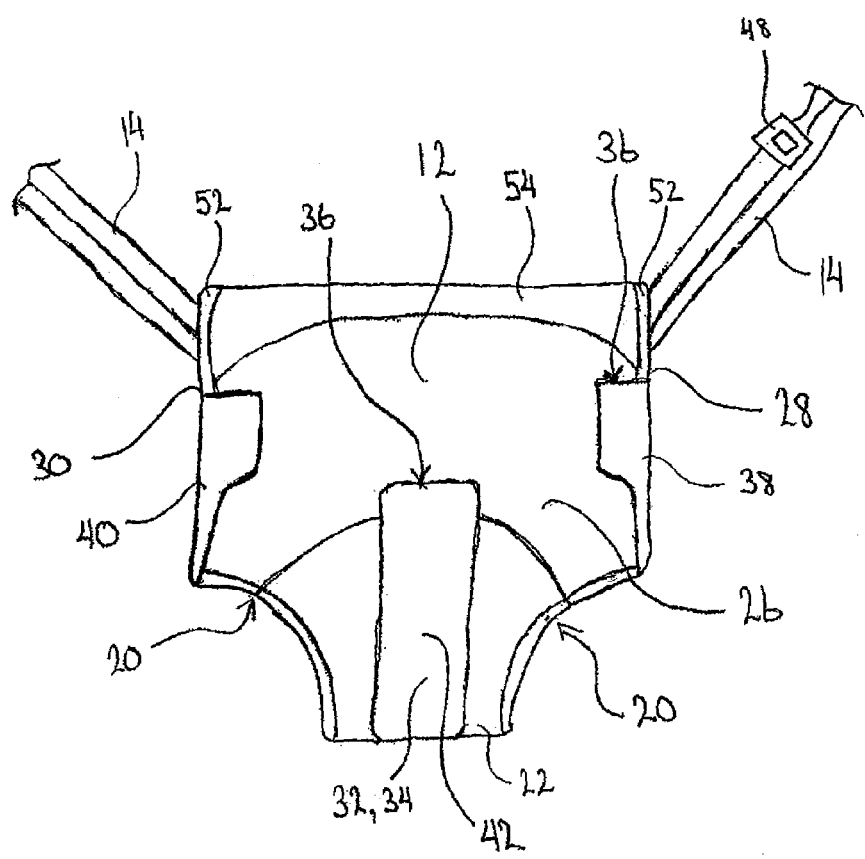
FIG. 3 shows a rear view of the shoulder brace of FIG. 2.

With general reference to FIGS. 1-3, the girdle 12 is configured as a short pant. Thus, the girdle 12 is comprised of a flexible cloth material that may be worn as a garment by the human, with the human's legs extending through the girdle 12 and the girdle 12 fitting around the pelvis of the human. Accordingly, the girdle 12 may extend from the human's waist down to his or her legs. In one embodiment, the girdle 12 is comprised of a spandex material or any of numerous other cloth materials commonly used for athletic girdles. Of course, one of skill in the art will recognize that numerous other girdle configurations and materials are may be used for the girdle. For example, the girdle 12 could be configured as a long pant made of cotton.

The girdle 12 shown in FIGS. 1-3 defines two leg holes 20 which are separated by a crotch portion 22. When the human wears the girdle 12, the human's legs extend through the leg holes 20 and the crotch portion 22 is positioned between the legs. The girdle 12 further includes a front portion 24, a rear portion 26, a right side portion 28, and a left side portion 30. The front portion 24 is worn on the front of the human and the rear portion 26 is worn on the back of the human. Likewise, the right portion 28 is worn on the right side of the human and the left portion 30 is worn on the left side of the human.

In one preferred embodiment, the girdle 12 is configured as a football girdle. Accordingly, the girdle 12 includes a plurality of pad holders 32 designed to retain pads, and particularly football pads. As shown in FIGS. 1-3, the pad holders 32 are pockets 34 sewn on or otherwise provided on the girdle 12. The pockets 34 generally conform to the shape of the pad to be received. The pockets 34 may include openings 36 configured for insertion and removal of the pads. In one embodiment, the openings 36 are positioned near the top of the pocket, allowing the pad to be inserted downward into the pocket. However, the openings 36 may be configured otherwise, as will be recognized by those of skill in the art. For example, an opening in a pocket may be configured using vertical slits in the pockets.

In other embodiments, the pad holders 32 are configured differently. For example, the pockets 36 may be designed without openings. In this embodiment, the pads are completely contained within the pockets and may not be removed from the pockets.

Other types of pad holders are also possible, such as snaps positioned on the sides of the girdle. In this embodiment, the snaps are arranged and positioned to engage complementary snaps on the pads. In another exemplary embodiment, the pad holders are configured as hook and loop type fasteners, such as a Velcro® strips. One portion of the hook and loop fastener is secured to the girdle and the other portion of the hook and loop fastener is secured to the pad. When the pad is brought into contact with the pad holder on the girdle, the pad is retained in position on the girdle.

The pad holders 32 are configured to retain various types of pads, including hip pads and buttocks pads. To this end, the pad holders include a right hip pad holder 38, left hip pad holder 40, and a buttocks pad holder 42. The pad holders 32 are typically secured to the girdle 12 using reinforced stitching. The use of reinforced stitching provides additional support for the pad holder, allowing the pad holder to better withstand the rigors and strains of athletic activity, and particularly the game of football.

An athletic cup holder 44 may also be provided on the girdle 12. The athletic cup holder 44 is configured similar to the pad holders 32 described above, such that it receives an athletic cup and secures it in place on the girdle 12. Reinforced stitching is also used around the cup holder 44. Other pad holders or accessory holders on the girdle 12 are also contemplated, depending on the unique needs of a given athlete.

With continued reference to FIGS. 1-3, the tethers 14 are secured to the girdle 12. In particular, one end 50 of each tether 14 extends down the right side portion 28 or left side portion 30 of the girdle 12. The end 50 of each tether 14 is secured to the girdle 12 using reinforced stitching and additional fabric on a reinforced side area 52. This reinforced side area 52 is intended to provide additional support for the tethers 14, allowing the tethers 14 to be more securely fastened to the girdle 12, and preventing tearing of the girdle 12 during athletic activity. However, in other embodiments, the tethers 14 are secured to the girdle using other fastening means, such as adhesives, hook and loop fasteners, rivets, or other fastening means, as are known in the art. The reinforced side area 52 is also attached to a reinforced waistband 54, providing additional strength to the girdle 12.

The tethers 14 are generally long straps that extend from the girdle 12. The tethers 14 are typically made of strips of flexible cloth material, such as thick cotton, polyester, or other relatively strong material. In other embodiments, the tethers 14 may be comprised of other flexible materials as are known to those of skill in the art. The tethers may also take other forms, such as ropes secured to the girdle 12.

The tethers 14 are typically ten or more inches in length, and less than thirty-six inches in length. The length of the tethers 14 will depend on the size of the individual and the desired degree of arm movement restriction. In one embodiment, the tethers are adjustable in length. In this embodiment, an adjustment means is provided on the tether, such as a buckle 48, as shown in FIG. 3. The adjustment means allows the tether to extend between a short length and a long length to accommodate different individuals with different shoulder injuries.

The tethers 14 may be provided on only one side or both sides of the girdle 12. Tethers 14 are provided on the right side portion 28 of the girdle 12 for use with a right shoulder injury. Tethers 14 are provided on the left side portion 30 of the girdle 12 for use with a left shoulder injury. Tethers 14 are provided on both side portions 28 and 30 in the event of injury to both the left and right shoulder.

In addition to a tether 14 fastened to either or both sides of the girdle 12, one or more tethers 14 may be provided on a given side. A single tether 14 may be used to restrict movement of an arm, while multiple tethers 14 on the same side will provide further strength to the tether, better insuring restricted arm movement. Two tethers 14 may also be used to more evenly restrict arm movement. For example, a first tether may extend to a front side of the arm, while a second tether may extend to a back side of the arm, thus evenly distributing the forces applied to the arm. In one embodiment, two or more tethers may also be used to provide for adjustment of the tether length. In this embodiment, one tether is secured to the girdle 12 and another tether is secured to the arm. A buckle is positioned between the tethers, allowing the effective distance of the tethers from girdle to arm to be adjusted. Furthermore, while only two tethers 14 are shown in the embodiments of FIGS. 1-3, three or more tethers may also be used.

While one end 50 of the at least one tether 14 is fastened to the girdle 12, an opposite end 60 of the at least one tether is fastened to the arm band 16. In one embodiment, the arm band 16 is integral with the tether 14 and formed on the opposite end 60 of the tether. Thus, in the embodiment of FIG. 2, the opposite end 60 of the tether 14 includes a hook and loop type fastener. The hook members 62 are provided on one portion of the opposite end 60 of the tether 14 and the loop fasteners 64 are provided on another portion of the tether. When the end of the tether 14 is wrapped around the athlete's arm, and the hook members 62 are brought into contact with the loop fasteners 64, an arm band is formed around the arm. With the arm band 16 positioned around the athlete's arm, and the tether 14 extending between the arm band 16 and the girdle 12, movement of the arm is restricted based on the length of the tether 14. While hook and loop type fasteners have been disclosed for use in forming the arm band 16 at the end of the tether 14, other types of fasteners may be used to form the arm band such as snaps or other fasteners as will be recognized by those of skill in the art.

FIGS. 4-6 disclose an embodiment where the arm band 16 is provided separate from the tether 14. In this embodiment, the arm band 16 is formed as a strip of fabric or other flexible material. The strip of fabric is designed with a width of about two to six inches, and a length of about eight inches to sixteen inches, or more, depending on the size of the athlete. The width of the strip generally makes the arm band more comfortable for the individual, with a wider armband distributing pulling forces on the arm band more evenly over the arm. The length of the armband 16 is highly dependant on the size of the individual. In one embodiment, the armband 16 is designed to extend around the bicep of the individual, and the length of the arm band 16 must be sufficiently long to completely encompass the bicep with some overlapping material.

The material used for the arm band 16 may be any of numerous materials as are known in the art. For example, the arm band may be made of cotton, polyester, spandex, or any other flexible fabric or material. In one embodiment, the material includes a resilient quality, such as spandex, allowing the arm band to be stretched and then returned to its original shape. Such resilient fabrics are useful if the individuals arm will be bent or if arm muscles will be flexed during athletic activity.

As shown in FIGS. 4 and 5, the arm band 16 includes a fastener 70 that allows the arm band to be wrapped around the arm. For example, if a hook and loop type fastener is used, the arm band includes a hook portion 74 on one side and end of the arm band 16, and a loop portion 72 on an opposite side and end of the arm band. The end loop portion 72 is shown in FIG. 4, next to a central loop portion 78. The hook portion 74 of the arm band is provided on an end of the band opposite surface 76. When the surface of the arm band that is opposite the loop portions 72, 78 is contacted with the skin on the arm, the hook portion 74 of the arm band is wrapped around the arm and brought into contact with the loop portion 72. This forms a secure band around the arm, and the exposed central loop portion 78 provides a surface for attachment of the tether. If the arm band 16 is comprised of a flexible fabric material, the arm band will fit snugly against the arm yet allow for expansion of the arm band when muscles are flexed.

After the arm band 16 is secured to the arm, the tethers 14 are secured to the arm band 16. As shown in FIG. 6, the tethers 14 extend all the way to the arm band 16. The end 60 of each tether includes a fastener, such as a hook portion 64 of a hook and loop arrangement. The hook portion 64 of the tether is brought into contact with and wrapped around the central loop portion 78 of the arm band. This effectively fastens the tether to the arm band 16. With the tether fastened to the arm band 16, the arm band is restricted from moving further than the length of the tether away from the girdle. Thus, when an athlete wears the shoulder brace, arm movements and associated shoulder movements are restricted by the length of the tether.

The shoulder brace disclosed herein is particularly compatible for use by a football player wearing a football uniform. The tethers 14 extending from the football girdle 12 may extend under a player's jersey to the arms. Alternatively, the player's jersey may be tucked into the girdle 12 and the tethers 14 may be routed outside of a player's jersey to the arms. The particular arrangement used by the player may depend on certain league rule that must be followed. Advantageously, the shoulder brace 10 may be comfortably worn and does not contact the player's chest. Thus, heavy breathing by the football player does not make the shoulder brace uncomfortable or problematic. In addition, because the tether is fastened to a girdle, the brace is prevented from riding upon on the player's torso. Furthermore, the fastening arrangement between the tether and the girdle does not result in a wedge effect during use.

Although the present invention has been described with respect to certain preferred embodiments, it will be appreciated by those of skill in the art that other implementations and adaptations are possible. For example, while certain materials have been listed as possible materials for various parts of the shoulder brace, other materials are possible without departing from the spirit and scope of the invention. Furthermore, different fastening means and arrangements have been disclosed, both other fastening means and arrangements are possible without departing from the spirit and scope of the invention. Moreover, there are advantages to individual advancements described herein that may be obtained without incorporating other aspects described above. Therefore, the spirit and scope of the appended claims should not be limited to the description of the preferred embodiments contained herein.

What is claimed is:

1. A shoulder brace comprising:
   a football girdle including a crotch portion and a plurality of pockets including a left pocket on a left side of the girdle and a right pocket on a right side of the girdle;
   a left hip pad positioned in the left pocket and a right hip pad positioned in the right pocket;
   a plurality of tethers including two left tethers connected to the left side of the girdle in the region of the left pocket and two right tethers connected to the right side of the girdle in the region of the right pocket;
   a left upper-arm band connected to at least one of the two left tethers, the left upper-arm band configured to surround a portion of a person's left arm between an elbow and a shoulder such that the shoulder brace restricts movement of the left arm; and
   a right upper-arm band connected to at least one of the two right tethers, the right upper-arm band configured to surround a portion of a person's right arm between an elbow and a shoulder such that the shoulder brace restricts movement of the right arm.

2. The shoulder brace of claim 1 wherein each tether is at least 10 inches in length.

3. The shoulder brace of claim 1 wherein each tether is adjustable in length.

4. The shoulder brace of claim 1 wherein the girdle includes at least one pad holder.

5. The shoulder brace of claim 4 wherein the plurality of pockets are configured to retain an athletic cup.

6. The shoulder brace of claim 1 further comprising at least one football buttocks pad positioned in the plurality of pockets.

7. The shoulder brace of claim 1 wherein each tether is fastened at one end to an upper side portion of the girdle and at an opposite end to the upper arm band, wherein the upper side portion of the girdle is a portion of the girdle located between a top edge of the girdle and one of the plurality of pockets.

8. The shoulder brace of claim 1 wherein the left upper arm band comprises a strap configured to extend around a human arm.

9. The shoulder brace of claim 8 wherein the strap includes a hook and loop material.

10. A shoulder brace of claim 1 wherein the girdle is configured as a pant designed to fit around a man's pelvis and legs.

11. The shoulder brace of claim 10 wherein the pant is designed to extend from the man's waist to his hips.

12. The shoulder brace of claim 10 wherein each tether extends downward along a reinforced side portion of the girdle and is connected to the girdle along the reinforced side portion, wherein the reinforced side portion extends to one of the pockets.

13. The shoulder brace of claim 1 wherein the left upper arm band is integral with the at least one of the two left tethers.

14. A shoulder brace for restricting movement of the arm of a human, the shoulder brace comprising:
- a girdle comprising a waist portion and a plurality of hip pad holders, the plurality of hip pad holders including a left hip pad holder on a left side of the girdle and a right hip pad holder on a right side of the girdle;
- a left hip pad positioned in the left hip pad holder and a right hip pad positioned in the left hip pad holder;
- at least one tether attached to the left side or the right side of the girdle, the tether including a distal end configured to extend around the arm of the human above the elbow and a proximal end attached to the girdle between the waist portion and one of the hip pad holders such that a length of the proximal end of the tether extends downward along the girdle between the waist portion and the one of the hip pad holders, the tether being flexible along the substantial length of the tether, wherein the tether of the shoulder brace restricts movement of the arm of the human when the human wears the girdle and extends the distal end of the tether around the arm above the elbow such that the distal end of the tether is retained upon the arm.

15. The shoulder brace of claim 14 further comprising an arm band connected to the one end of the at least one tether, wherein the arm band is designed to engage the arm of the human.

16. The brace of claim 14 wherein the girdle comprises a pant.

17. The brace of claim 14 wherein the arm band is at least 10 inches removed from the girdle when the tether is extended away from the girdle.

18. A shoulder restraining device for an athlete, the retraining device comprising:
- a pant member including an upper edge;
- at least one pad holder provided on the pant member;
- at least one pad positioned in the pad holder; and
- means attached to the pant member for holding at least one of the athlete's arms in proximity to the pant such that the amount of movement possible by the arm is restricted, wherein the means for holding at least one of the athlete's arms includes at least two tethers on each side of the pant member, each tether connected to the pant member at a position located at or between the pad holder and the upper edge of the pant member.

19. The shoulder restraining device of claim 18 wherein the pant member is a short pant.

* * * * *